United States Patent
Kubo

(10) Patent No.: US 6,958,413 B2
(45) Date of Patent: Oct. 25, 2005

(54) METHOD OF REACTION WITH SOLUBLE METALLIC CATALYST AND ANION-EXCHANGE RESIN, METHOD OF RECOVERING THE SOLUBLE METALLIC CATALYST, AND METHOD OF REUSE

(75) Inventor: Takafumi Kubo, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 10 days.

(21) Appl. No.: 10/104,054

(22) Filed: Mar. 25, 2002

(65) Prior Publication Data

US 2002/0198403 A1 Dec. 26, 2002

(30) Foreign Application Priority Data

Mar. 26, 2001 (JP) .................................... P.2001-087846

(51) Int. Cl.[7] .......................... C07C 67/26; C07C 67/24
(52) U.S. Cl. ...................................... 560/209; 560/240
(58) Field of Search .................................. 560/209, 240

(56) References Cited

U.S. PATENT DOCUMENTS 4,069,242 A * 1/1978 Gurgiolo
4,417,077 A * 11/1983 Drago et al.

FOREIGN PATENT DOCUMENTS

| EP | 1 029 847 A1 | 8/2000 |
| JP | 46-4970 | 11/1971 |
| JP | 54-100307 | 8/1979 |
| JP | 9-262479 | 10/1997 |

OTHER PUBLICATIONS

International Search Report.

* cited by examiner

Primary Examiner—Paul A. Zucker
(74) Attorney, Agent, or Firm—Sughrue Mion, PLLC

(57) ABSTRACT

The invention provides a method of liquid-phase reaction using a soluble metallic catalyst in which the soluble metallic catalyst is caused to coexist with an anion-exchange resin during the reaction and the reaction is conducted under such conditions that 50% or more of the soluble metallic catalyst is adsorbed onto the anion-exchange resin. The anion-exchange resin having the soluble metallic catalyst adsorbed thereon is separated from the liquid reaction mixture to thereby recover the soluble metallic catalyst and reuse it in a liquid-phase reaction. The soluble metallic catalyst is efficiently used, recovered, and reused with great ease at low cost in various liquid-phase reactions using the soluble metallic catalyst.

9 Claims, No Drawings

METHOD OF REACTION WITH SOLUBLE METALLIC CATALYST AND ANION-EXCHANGE RESIN, METHOD OF RECOVERING THE SOLUBLE METALLIC CATALYST, AND METHOD OF REUSE

TECHNICAL FIELD

The present invention relates to a method of liquid-phase reaction using a soluble metallic catalyst and an anion-exchange resin, a method of recovering the soluble metallic catalyst, and a method of reusing the recovered soluble metallic catalyst in a liquid-phase reaction.

BACKGROUND ART

Compounds containing metallic elements have hitherto been used as catalysts for various reactions. In liquid-phase reactions, compounds such as metal salts and metal complexes, among those catalyst compounds, are frequently used as catalysts in the state of being dissolved in the liquid reaction mixture (hereinafter, these compounds are referred to as "soluble metallic catalysts"). These soluble metallic catalysts generally are highly selective catalysts having high activity because they act in a dissolved state. However, since these catalysts are difficult to separate from the liquid reaction mixtures, they are discarded after use or require much labor or cost for separation/recovery.

An example of such liquid-phase reactions is a process for producing 2-hydroxyethyl acrylate by causing ethylene oxide to add to acrylic acid with the aid of a chromium compound as a soluble metallic catalyst. If the chromium compound in this process can be easily separated and recovered and be reused, considerable environmental and economical merit can be expected.

Various techniques are known for the separation/recovery of soluble metallic catalysts. Examples thereof include a method in which after a reaction the reaction product is taken out by distillation and the catalyst is recovered as a distillation bottom and a method in which a catalyst is recovered by an extraction operation. However, these techniques pose a problem concerning accumulation of a by-product, or necessitate complicated steps and enlarged apparatus, leading to a cost increase.

Also known is a technique in which an ion-exchange resin is used to recover a soluble metallic catalyst. Japanese Patent Laid-Open No. 44300/1984 discloses a method in which after phthalic acid is reacted with an epoxy compound with the aid of a chromium compound as a soluble metallic catalyst, the resultant liquid reaction mixture is dissolved in a solvent, e.g., water, and the catalyst is recovered with a cation-exchange resin. Although this method can be used for catalyst recovery, it has drawbacks that use of a solvent is necessary for the recovery and that a special eluent and much labor are required for reusing the catalyst adsorbed onto the cation-exchange resin.

Japanese Patent Laid-Open No. 152246/1999 discloses a method of catalyst recovery in a process for producing an aromatic carboxylic acid with the aid of a cobalt catalyst. This method uses a chelate type anion-exchange resin for the recovery. Although this method is effective in efficiently recovering the catalyst, a catalyst adsorption step which takes much time and a desorption step are necessary separately from the reaction step.

As described above, the related-art methods of catalyst recovery with an ion-exchange resin have had problems that the reuse of the catalyst adsorbed onto the ion-exchange resin necessitates much labor and that the process is complicated and requires much time because of the necessity of a catalyst adsorption step and a catalyst desorption step separately from the reaction step.

A process in which a combination of a zeolite, which is a solid acid catalyst, and a tin compound serving as a soluble metallic catalyst is used in the esterification reaction of octanoic acid with pentaerythritol is discussed in *Heisei 10-nen Jisedai Kagaku Purosesu Gijutsu Kaihatsu Seika Hôkoku-sho*, pp.395–422 (Japan Chemical Industry Association). In this process, the zeolite functions not only as a catalyst but as an adsorbent for the tin compound and, hence, the tin compound can be easily recovered/reused. However, this process is usable in limit applications because zeolites dissolve in strong acids or alkalis and because in some reactions, zeolites may cause undesirable side reactions, e.g., ring-opening polymerization of epoxy compounds, due to the acid sites thereof. Furthermore, since the adsorption of the tin compound onto the zeolite is not based on ion exchange, the tin compound adsorbed readily passes away upon cleaning with hexane. Consequently, the zeolite cannot be cleaned while keeping the catalyst held thereon and, hence, it has been difficult to produce a variety of products with the same catalyst system.

On the other hand, U.S. Pat. No. 4,069,242 (corresponding to Japanese Patent Publication No. 25421/1986) describes a process for producing an ester, e.g., 2-hydroxyethyl acrylate, in which a chromium (or iron) compound and an organic amine compound are used in combination as a catalyst. The use of these two catalyst compounds in combination in this process is intended to produce a synergistic effect in the rate of reaction and the yield of the target compound. There is no description therein concerning the separation/recovery of a soluble metallic catalyst with an anion-exchange resin. Although the Examples given therein contain a statement to the effect that an iron compound was used in combination with an anion-exchange resin, the degree of adsorption of the iron compound onto the anion-exchange resin is presumed to be below 50%. The actual effect of recovery in this related-art process is low.

Soluble metallic catalysts are usually discarded frequently. However, discard is undesirable from the standpoints of profitability and environment, and there is a desire for a method for easily recycling soluble metallic catalysts.

As described above, the recovery/reuse of a soluble metallic catalyst in various liquid-phase reactions in the related art has had drawbacks that much labor or a large equipment is required and the process is complicated and takes much time. Furthermore, the technique in which a soluble metallic catalyst and a zeolite are used in combination has been usable in limited applications because of the problems attributable to the nature of zeolites and because the metallic catalyst dissolves away upon cleaning.

Accordingly, the invention has been achieved in view of the problems of the above described techniques of the related art. An aim of the invention is to provide a method of reaction using a soluble metallic catalyst and an anion-exchange resin in which the soluble metallic catalyst can be efficiently used, recovered, and reused with great ease at low cost. Another aim of the invention is to provide a method of recovering the soluble metallic catalyst and a method of reusing the catalyst recovered.

DISCLOSURE OF THE INVENTION

As a result of intensive investigations made by the present inventors, it has been found that in a liquid-phase reaction using a soluble metallic catalyst, the soluble metallic catalyst can be efficiently used, recovered, and reused with great ease at low cost by using an anion-exchange resin under specific conditions. The invention has been completed based on this finding. The invention has the following constitutions.

(1) A method of liquid-phase reaction using a soluble metallic catalyst which comprises causing the soluble metallic catalyst to coexist with an anion-exchange resin during the reaction and conducting the reaction under such conditions that 50% or more of the soluble metallic catalyst is adsorbed onto the anion-exchange resin.

(2) A method of recovering a soluble metallic catalyst which comprises separating from the liquid reaction mixture the anion-exchange resin having the soluble metallic catalyst adsorbed thereon by the method (1).

(3) A method of reusing a soluble metallic catalyst which comprises reusing in a liquid-phase reaction the soluble metallic catalyst recovered by the method (2).

(4) A process for producing a hydroxy ester of a carboxylic acid from the carboxylic acid and an epoxy compound by the method (1).

In various liquid-phase reactions conducted in the presence of both a soluble metallic catalyst and an anion-exchange resin, a phenomenon is observed in which the soluble metallic catalyst is gradually adsorbed onto the anion-exchange resin with progress of the reaction. This phenomenon is thought to be attributable to the compositional change of the liquid reaction mixture with progress of the reaction. In this method, since the reaction and the adsorption of the soluble metallic catalyst occur simultaneously, the soluble metallic catalyst can be easily recovered from the reaction products after the reaction by merely separating the anion-exchange resin from the liquid reaction mixture.

After the anion-exchange resin having the soluble metallic catalyst adsorbed thereon is thus separated from the liquid reaction mixture, starting materials are introduced into a system containing the anion-exchange resin. As a result, the soluble metallic catalyst is desorbed from the anion-exchange resin and becomes free and reusable for reactions. Thus, the soluble metallic catalyst can be repeatedly used. Namely, by merely using the anion-exchange resin having a soluble metallic catalyst adsorbed thereon to conduct the subsequent reaction operation, the same reaction as in the case of adding a soluble metallic catalyst can be realized.

Since the invention does not necessitate the complicated steps of adsorption and desorption as described above, a soluble metallic catalyst can be easily used, recovered, and reused through simple steps at low cost.

Furthermore, by suitably selecting the amounts of the soluble metallic catalyst and the anion-exchange resin and thereby changing the free state/adsorbed state proportion for the soluble metallic catalyst, the rate of reaction can be controlled.

The effects of the invention are significant especially in the addition reaction of epoxy compounds with carboxylic acids using a soluble metallic catalyst. The mechanism of the adsorption of the soluble metallic catalyst in this reaction is presumed to be as follows. The metal ion of the soluble metallic catalyst in a dissolved state forms a complex containing as a ligand the anion derived from the carboxylic acid. In the case where the liquid reaction mixture has a high carboxylic acid concentration, ligands are present in a high concentration in the liquid reaction mixture and, hence, the complex is present in the liquid reaction mixture. On the other hand, since the exchange groups of the anion-exchange resin (counter anions in the case of exchange groups of a salt structure) generally have coordinating properties, inner parts of the anion-exchange resin are thought to be an environment in which ligands are present in a high concentration. As the reaction proceeds, the concentration of the carboxylic acid becomes low and the ligand concentration in the liquid reaction mixture decreases accordingly. In the anion-exchange resin, however, ligands are present in a high concentration. Consequently, the complex is thought to move into the anion-exchange resin and be adsorbed.

Factors which influence the degree of adsorption of a soluble metallic catalyst onto an anion-exchange resin are thought to include ligand concentration and the strength of coordinate force. The lower the ligand concentration in the liquid reaction mixture and the higher the coordinate force, the higher the degree of adsorption. The reason why higher coordinate forces result in higher degrees of adsorption may be that the higher coordinate forces enable the complex to be present stably. When the reaction product is apt to coordinate, the soluble metallic catalyst is less apt to be adsorbed because the product also coordinates to the catalyst. Conversely, when the reaction product is less apt to coordinate, the soluble metallic catalyst is apt to be adsorbed, resulting in an improved catalyst recovery.

The phenomenon in which when a reaction is conducted in the presence of both a soluble metallic catalyst and an anion-exchange resin, the soluble metallic catalyst is adsorbed onto the anion-exchange resin with progress of the reaction is presumed to occur by the mechanism described above.

Even when the contact of the anion-exchange resin with a liquid reaction mixture containing the soluble metallic catalyst is initiated at the time of initiation of the reaction or at any time in the course of the reaction, the soluble metallic catalyst present in the liquid reaction mixture can be adsorbed by the mechanism described above. In the invention, there are no limitations in this respect as long as the reaction and the adsorption of the catalyst proceed simultaneously. From the standpoint of the simplification of steps, simultaneously conducting the reaction and adsorption is considerably significant.

A feature of the invention resides in that the degree of adsorption of the soluble metallic catalyst onto the anion-exchange resin is 50% or higher. The degree of adsorption of 50% or higher is advantageous in that problems attributable to a residual catalyst (e.g., increase in by-product amount) are less apt to arise in a purification step after the reaction. Another advantage is that especially when the degree of adsorption is high, it is possible to put the reaction product into the market without via a purification step. Furthermore, by adsorbing 50% or more of the soluble metallic catalyst and recovering/reusing the catalyst adsorbed, the catalyst cost and the amount of wastes are reduced. Thus, economical and environmental effects can be sufficiently obtained.

In the method described hereinabove in which a soluble metallic catalyst and a zeolite are used in combination, the tin compound adsorbed dissolves away upon hexane extraction. This may be because the octanoate ions and chloride ions which participate in the adsorption dissolve away. In the invention, the ligand ingredient participating in adsorption does not dissolve away because it is bonded to the anion-exchange resin through ionic bonds or covalent bonds. Consequently, even when the anion-exchange resin having the soluble metallic catalyst adsorbed thereon is cleaned with a non-coordinating solvent such as hexane, the soluble metallic catalyst hardly dissolves away. Because cleaning can be conducted without causing dissolution, the same catalyst can be easily used for the production of a variety of products.

Furthermore, the anion-exchange resin functions also as a basic catalyst. Consequently, in the above-described reaction of a carboxylic acid with an epoxy compound, the resin functions also as a catalyst to accelerate the reaction. The anion-exchange resin does not cause side reactions such as those accompanying the use of zeolites (e.g., ring-opening polymerization of epoxy compounds). In case where a side reaction occurs due to the activity of the anion-exchange resin, the activity thereof can be regulated by changing the basicity of the counter anions. Ion-exchange resins further have an advantage that they do not dissolve in strong acids or bases.

According to the invention, a soluble metallic catalyst can be efficiently used, recovered, and reused with great ease at low cost as described above. The invention is hence effective especially in the recovery and reuse of heavy metal elements and noble metal elements, which is highly desired from the standpoints of the environment and profitability. It has also become possible to use the catalyst in an increased amount, although increasing the catalyst amount has been limited for environmental and economical reasons. As a result, an improvement in selectivity, reduction in reaction time, and reduction in reaction temperature can be attained. The invention is hence effective also from the standpoint of reaction.

BEST MODE FOR CARRYING OUT THE INVENTION

The invention will be explained in detail below.

The anion-exchange resin usable in the invention is a resin having an anion-exchange ability. Examples thereof include resins having an amine and/or a quaternary ammonium salt as exchange groups, resins having pyridine and/or a pyridinium salt as exchange groups, and resins having a phosphine and/or a quaternary phosphonium salt as exchange groups.

The anion-exchange resin to be used in the invention can be one suitably selected according to the reaction to which the invention is applied. However, it is preferred to use any of resins containing a quaternary ammonium salt and resins containing a quaternary phosphonium salt because the degree of adsorption of soluble metallic catalysts onto these resins is high. More preferred of these are ones having high liquid permeability and high heat resistance. Specifically, a styrene-based anion-exchange resin in which a quaternary ammonium salt as exchange groups is bonded to the matrix through an alkylene group having 4 or more carbon atoms and an anion-exchange resin obtained by polymerizing and solidifying diallyldimethylammonium chloride are preferred.

The amount of the anion-exchange resin to be used is preferably such that the anion-exchange capacity thereof corresponds to from 1 to 1,000 times by mole the amount of the soluble metallic catalyst. The volume of the anion-exchange resin is preferably in the range of from 1 to 70% based on the total volume of the liquid reaction mixture, and is more preferably in the range of from 5 to 30% thereof. The type of the exchange groups of the anion-exchange resin can be suitably selected, and may be the acid neutralization type or free type (in the case of exchange groups of a salt structure, the counter anions may be of either type). However, the exchange groups are preferably ones which do not yield a by-product during the reaction.

Examples of liquid-phase reactions to which the invention is applicable include an oxidation reaction, reduction reaction, condensation reaction, esterification reaction, amidation reaction, etherification reaction, carbonylation reaction, alkylation reaction, and hydroformylation reaction. Reactions for which the invention is especially suitable are reactions in which a Brønsted acid is used as a starting material. Specific examples of such reactions include esterification reactions in which a carboxylic ester is produced from a carboxylic acid and an alcohol, epoxy addition reactions in which a hydroxy ester of a carboxylic acid is produced from the carboxylic acid and an epoxy compound, and etherification reactions in which a glycol or hydroxyalkyl ether is produced from an alcohol and an epoxy compound. More preferred of these are the epoxy addition reactions in which a hydroxy ester of a carboxylic acid is produced from the carboxylic acid and an epoxy compound. More specifically, the invention is suitable for use in a reaction in which a hydroxy ester of (meth)acrylic acid is produced from (meth)acrylic acid and an alkylene oxide, in particular, a reaction in which hydroxyethyl (meth)acrylate is produced from (meth)acrylic acid and ethylene oxide.

In the case where the invention is used for reactions in which a Brønsted acid is used as a starting material, examples of usable Brønsted acids include carboxylic acid type compounds (e.g., alkanemono- or alkanedicarboxylic acids, aromatic mono- or dicarboxylic acids, and these acids substituted with hydroxy or a halogen, such as formic acid, acetic acid, propionic acid, butyric acid, caproic acid, stearic acid, (meth)acrylic acid, oxalic acid, malonic acid, succinic acid, adipic acid, maleic acid, itaconic acid, benzoic acid, phenylacetic acid, naphthenic acid, toluylic acid, phthalic acid, terephthalic acid, isophthalic acid, α-bromoglutaric acid, salicylic acid, p-chlorobenzoic acid, m-methoxybenzoic acid, β-hydroxybutyric acid, and poly((meth)acrylic acid)), phenol compounds (e.g., phenol, bisphenols, cresol, nonylphenol, xylenol, catechol, ethylphenol, naphthol, hydroquinone, and methoxyphenol), alcohol compounds (e.g., water, methanol, ethanol, propanol, butanol, octanol, ethylene glycol, propylene glycol, and allyl alcohol), and inorganic acid compounds (e.g., hydrochloric acid, hydrobromic acid, sulfuric acid, nitric acid, phosphoric acid, and hydrocyanic acid). Preferred Brønsted acids include carboxylic acid compounds and phenol compounds. More preferred are (meth)acrylic acid, terephthalic acid, succinic acid, and phenol. These compounds may be reacted alone or in combination of two or more thereof.

The term "soluble metallic catalyst" as used herein means a metallic catalyst which dissolves in the liquid reaction mixture and acts in the dissolved state. Although the soluble metallic catalyst to be used in the invention may be selected according to various reactions, it is preferred to use one which contains a metallic element tending to have a complex structure. Examples thereof include compounds containing chromium, iron, tin, manganese, cobalt, vanadium, titanium, nickel, zinc, copper, zirconium, molybdenum, tungsten, aluminum, lead, indium, ruthenium, rhodium, palladium, platinum, silver, or gold. Specific examples of such compounds include known halides, carboxylates, nitrates, sulfates, oxides, hydroxides, and complex compounds of those metals. In the invention, a system using a soluble metallic catalyst containing chromium, iron, cobalt, copper, ruthenium, rhodium, or palladium is preferred especially from environmental and economical standpoints.

Reaction conditions including reaction temperature, reaction time, starting material proportion, and catalyst amount may be selected according to various reactions. Especially with respect to reaction temperature, it is preferred to select conditions under which the anion-exchange resin is less apt to thermally deteriorate. Specifically, the preferred temperature range is from 20 to 140° C.

Examples of methods for conducting a reaction while causing a soluble metallic catalyst and an anion-exchange resin to coexist with each other include (A) a method in which the two ingredients are placed in a single reactor and the reaction and adsorption are conducted therein and (B) a method in which a resin vessel containing the anion-exchange resin is separately disposed and a liquid reaction mixture is circulated through the vessel to conduct the reaction and adsorption. In the case where a resin vessel is separately disposed, this vessel may be either a fixed-bed or suspended-bed vessel. The coexistence of the anion-exchange resin with a liquid reaction mixture containing the soluble metallic catalyst may be initiated at the beginning or in the course of the various reactions as stated above. The coexistence of these may be terminated before completion of the reaction, or may be continued until completion of the reaction. From the standpoint of apparatus simplicity, it is preferred to employ method (A) to conduct a reaction and adsorption while causing the two ingredients to coexist from the beginning to completion of the reaction. In the case of conducting a reaction which emits a large amount of heat, it is preferred from the standpoint of heat removal to employ method (B) so that the coexistence of the two ingredients and adsorption are initiated in the course of the reaction. Method (B) is advantageous also in that the separation of the resin from the liquid reaction mixture is easy.

The term "degree of adsorption" as used for the adsorption of a soluble metallic catalyst onto an anion-exchange resin means the proportion of the amount of the soluble metallic catalyst which has been adsorbed onto the anion-exchange resin to the total amount of the soluble metallic catalyst present in the reaction system.

In the invention, the degree of adsorption of the soluble metallic catalyst onto the anion-exchange resin should be 50% or higher so as to heighten the effect of catalyst recovery. The degree of adsorption thereof is preferably 70% or higher, more preferably 90% or higher.

Examples of techniques for improving the degree of adsorption of a soluble metallic catalyst onto an anion-exchange resin include a method in which the conversion of a starting material is heightened to thereby lower the concentration of the starting material, a method in which an ingredient forming a stabler complex is added, and a method in which a solvent is added. These techniques can be used in suitable combination to attain the desired degree of adsorption. The conversion of a starting material is preferably 70% or higher, more preferably 90% or higher. Preferred examples of the ingredient forming a stabler complex include low-molecular coordinating compounds such as acetic acid and propionic acid and coordinating compounds forming a chelate ring, such as oxalic acid, succinic acid, malic acid, salicylic acid, ethylenediamine, iminodiacetic acid, and ethylenediaminetetraacetic acid. The solvent to be added is preferably an inert one. Examples thereof include hexane, cyclohexane, toluene, acetone, methyl ethyl ketone, and cyclohexanone.

For determining the degree of adsorption, a general method may be used. Examples thereof include a method in which the concentration of free metal ions in the liquid reaction mixture is measured by, e.g., absorption spectrometry for ultraviolet and visible region, atomic absorption spectrometry, or ICP emission spectroscopy and the degree of adsorption is determined from the found value of concentration. In the case where the degree of adsorption increases with progress of the reaction, the degree of progress of the reaction can be determined from the degree of adsorption.

Techniques for separating the anion-exchange resin from the liquid reaction mixture are not particularly limited. Examples thereof include filtration with a mesh, filter fabric, or strainer, decantation, and distillation. The anion-exchange resin need not be completely separated from the liquid reaction mixture, and starting materials may be added after partial removal of the liquid reaction mixture.

In the case where the anion-exchange resin having a soluble metallic catalyst adsorbed thereon is to be reused, a method may be employed which comprises separating the anion-exchange resin from the liquid reaction mixture, adding starting materials thereto, and then immediately using the resultant mixture to conduct the subsequent operation of reaction. Alternatively, a method may be employed in which the anion-exchange resin is cleaned with a solvent and then used for the subsequent operation of reaction. In the case of conducting cleaning, the cleaning solvent is preferably one having such relatively low coordinating properties that the soluble metallic catalyst does not dissolve away. Examples of the solvent include linear alkanes, branched alkanes, aromatic compounds, ester compounds, and ketone compounds. Specific examples thereof include n-hexane, n-heptane, cyclohexane, toluene, xylene, methyl acetate, ethyl acetate, butyl acetate, acetone, and methyl ethyl ketone. After having been cleaned with a solvent, the anion-exchange resin may be used as it is for the subsequent operation of reaction or may be used after solvent volatilization. In reusing the anion-exchange resin having the catalyst adsorbed thereon, a reaction may be initiated immediately after starting materials are added thereto. Alternatively, a reaction may be initiated after starting materials are added and the soluble metallic catalyst is sufficiently eluted from the anion-exchange resin. Preferably, the reaction is initiated after at least 50%, more preferably at least 80%, and most preferably at least 90% of the soluble metallic catalyst adsorbed on the anion-exchange resin has been eluted. Examples of techniques for elution include a method in which the anion-exchange resin is mixed with starting materials in a single reactor to thereby elute the soluble metallic catalyst and a method in which a starting material is passed through a resin vessel to elute the soluble metallic catalyst.

The method of the invention is especially suitable for the production of a hydroxy ester of a carboxylic acid from the carboxylic acid and an epoxy compound. Carboxylic acids such as those enumerated above can be used in this reaction. Examples of the epoxy compound include ethylene oxide, propylene oxide, butylene oxide, butadiene oxide, styrene oxide, cyclohexene oxide, epichlorohydrin, epibromohydrin, epiiodohydrin, and mono-, di-, and polyglycidyl ethers. Preferred of these are ethylene oxide and propylene oxide.

In the case where the invention is applied to the reaction for producing a hydroxy ester of a carboxylic acid, examples of usable anion-exchange resins include resins having an amine and/or a quaternary ammonium salt as exchange groups, resins having pyridine and/or a pyridinium salt as exchange groups, and resins having a phosphine and/or a quaternary phosphonium salt as exchange groups. Since anion-exchange resins function also as catalysts, it is preferred to use an anion-exchange resin having high catalytic activity. Specifically, resins having a quaternary ammonium salt and resins having a quaternary phosphonium salt are preferred. More preferred of these are those having high heat resistance. Resins having a quaternary ammonium salt and resins having a quaternary phosphonium salt are preferred also because the degree of adsorption of soluble metallic catalysts thereonto is high. More specifically, a styrene-based anion-exchange resin in which a quaternary ammonium salt as exchange groups is bonded to the matrix through an alkylene group having 4 or more carbon atoms and an anion-exchange resin obtained by polymerizing and solidifying diallyldimethylammonium chloride are preferred.

The type of the exchange groups of the anion-exchange resin is preferably one which does not yield a by-product through the reaction. Specifically, the exchange groups are preferably ones whose counter ions are anions generated by the acid used as a starting material. For example, when the starting material is acrylic acid, the anion-exchange resin is preferably one in which the counter anions for the exchange groups are acrylate ions.

The reaction temperature is preferably from 20 to 140° C., more preferably from 50 to 100° C. The molar ratio of the epoxy compound to the carboxylic acid to be fed is preferably from 0.5 to 10.0, more preferably from 0.9 to 5.0, most preferably from 0.9 to 1.5. As the soluble metallic catalyst is preferably used a compound of trivalent chromium, compound of trivalent iron, or compound of trivalent ruthenium. Specific examples of such preferred catalysts include chromium acetate, chromium chloride, chromium nitrate, iron acetate, iron chloride, iron nitrate, ruthenium acetate, ruthenium chloride, and ruthenium nitrate. More preferred of these are the chromium compounds because they have high catalytic activity and the degree of adsorption thereof onto the anion-exchange resin is high. The amount of the catalyst to be used is preferably from 0.001 to 5% by mole based on the acid ingredient. The amount of the anion-exchange resin to be used is preferably such that the anion-exchange capacity thereof corresponds to from 1 to 1,000 times by mole the amount of the soluble metallic catalyst, and that the volume of the anion-exchange resin is in the range of preferably from 1 to 70%, more preferably from 5 to 30%, based on the total volume of the liquid reaction mixture.

In the reaction for producing a hydroxy ester of a carboxylic acid, examples of methods for conducting the reaction while causing a soluble metallic catalyst and an anion-exchange resin to coexist with each other include (A) a method in which the catalyst and the resin are placed in a single reactor and the reaction and adsorption are conducted therein and (B) a method in which a resin vessel is separately disposed and a liquid reaction mixture is circulated through the vessel to conduct the reaction and adsorption. In the case where a resin vessel is separately disposed, this vessel may be either a fixed-bed or suspended-bed vessel. The coexistence of the anion-exchange resin with a liquid reaction mixture containing the soluble metallic catalyst may be initiated at the beginning or in the course of the various reactions. The coexistence of these may be terminated before completion of the reaction, or may be continued until completion of the reaction. For improving the degree of adsorption, it is preferred that the contact of the two ingredients be initiated at the beginning or in the course of the reaction and continued until completion of the reaction. Specifically, the resin and the catalyst are kept in contact with each other over such a period that the conversion of the carboxylic acid increases preferably from 0 to 100%, more preferably from 50 to 100%, most preferably from 90 to 100%. From the standpoint of removing the heat of reaction, it is preferred to use the method in which a vessel containing the anion-exchange resin is separately disposed and a liquid reaction mixture is passed through the vessel and contacted with the resin while causing the reaction to proceed. This vessel is preferably of the fixed-bed type. In either case, the degree of adsorption of the soluble metallic catalyst should be 50% or higher for obtaining a sufficient effect in catalyst recovery. The degree of adsorption is preferably 70% or higher, more preferably 90% or higher.

Examples of techniques for improving the degree of adsorption of a soluble metallic catalyst onto an anion-exchange resin include a method in which the conversion of the acid is heightened to thereby lower the acid concentration, a method in which an ingredient forming a stabler complex is added, and a method in which a solvent is added. These techniques can be suitably used in combination to attain the desired degree of adsorption. The conversion of the acid is preferably 70% or higher, more preferably 90% or higher, most preferably 99% or higher. Preferred examples of the ingredient forming a stabler complex include low-molecular acids such as acetic acid, acrylic acid, and propionic acid and acids forming a chelate ring, such as oxalic acid, malonic acid, succinic acid, salicylic acid, malic acid, tartaric acid, citric acid, iminodiacetic acid, and ethylenediaminetetraacetic acid. The amount of this ingredient to be added is preferably up to 10%, more preferably up to 1%, based on the amount of the liquid reaction mixture. Such an acid is preferably added in the ending of the reaction because this timing of addition is highly effective. Specifically, the ingredient is added when the acid conversion has reached preferably 95% or higher, more preferably 99% or higher. The solvent to be added is preferably an inert one. Examples thereof include hexane, cyclohexane, toluene, acetone, methyl ethyl ketone, and cyclohexanone. The amount of the solvent to be added is preferably up to 70%, more preferably up to 40%, most preferably up to 20%, based on the amount of the liquid reaction mixture. The solvent may be added at the beginning or in the course of the reaction. However, it is preferred to add the solvent at the beginning of the reaction because this solvent addition may improve the selectivity to the target compound.

When the anion-exchange resin having the catalyst adsorbed thereon is to be reused, a method may be employed in which starting materials are added to the resin and the resultant mixture is used to immediately initiate a reaction. Preferably, however, the reaction is initiated after at least 50%, more preferably at least 80%, most preferably at least 90% of the catalyst adsorbed has been eluted. Examples of techniques for elution include a method in which the anion-exchange resin is mixed with starting materials in a single reactor to thereby elute the catalyst and a method in which a starting material is passed through a resin vessel to elute the catalyst.

The mechanism of catalyst separation/reuse by the method of the invention will be explained below in more detail with respect to an epoxy addition reaction, as an example, for producing 2-hydroxyethyl acrylate from acrylic acid and ethylene oxide.

When a chromium compound (e.g., chromium(III) acetate) is used as a catalyst and an anion-exchange resin of the quaternary ammonium type is caused to coexist therewith from the beginning of the reaction, then chromium(III) ions in a free state are present in the liquid reaction mixture in the initial stage of the reaction. The reaction proceeds due to the catalytic action of the chromium ions and anion-exchange resin. As the concentration of acrylic acid thus decreases, the adsorption of chromium(III) ions onto the anion-exchange resin proceeds. This phenomenon is thought to occur by the following mechanism. The chromium(III) ions are present in the form of a complex containing the anion of acrylic acid as the main ligand. As the acrylic acid concentration in the liquid reaction mixture decreases, the complex moves into the anion-exchange resin in which acrylic acid is present in a higher concentration. Thus, the adsorption proceeds. By merely separating this anion-exchange resin from the liquid reaction mixture after the reaction, the chromium ions can be easily recovered from the reaction product.

Upon introduction of acrylic acid into a reaction system comprising the anion-exchange resin having chromium ions thus adsorbed thereon, the chromium ions are desorbed from the anion-exchange resin and become free. Consequently, by merely adding to the subsequent reaction system the anion-exchange resin which has been used, the same reaction as that with addition of a chromium catalyst can be caused to occur. Namely, the chromium catalyst can be easily reused.

As described above, the soluble metallic catalyst used can be easily recovered and reused. Consequently, an increased catalyst amount can be used without exerting adverse influences on the environment. Therefore, not only selectivity to the target compound can be improved but also a reduction in reaction time, a reduction in reaction temperature, etc. can be attained. The method of the invention is hence advantageous also from the standpoint of profitability.

EXAMPLES

The invention will be explained below in greater detail by reference to Examples, but the invention should not be construed as being limited by these in any way. In the following Examples and Comparative Examples, all percents are by weight unless otherwise indicated.

Example 1

The effects of the invention were examined in a reaction for forming the hydroxypropyl ester of acrylic acid using chromium(III) acetate as a soluble metallic catalyst. First, 60 mg of chromium(III) acetate, 10.0 g of acrylic acid (AA), 10.0 g of propylene oxide (PO) (PO/AA molar ratio=1.2), and 0.66 g of an anion-exchange resin A (the anion-exchange resin disclosed in the Example 1 of Japanese Patent Application No. 2000-127664; produced by crosslinking a copolymer of diallyldimethylammonium chloride and diallylamine; having high heat resistance; used as a chloride ion type dry resin) were introduced into a 50 ml reactor made of pressure-resistant glass to give a reaction mixture. Subsequently, the reaction mixture was placed in a 60° C. thermostatic shaker and reacted with vigorous shaking. The reaction mixture was periodically sampled, and each sample was separated with a membrane filter into the resin A and a liquid reaction mixture, which was analyzed by gas chromatography to determine the progress of the reaction. The degree of adsorption of chromium ions onto the anion-exchange resin was determined from the absorbance (wavelength, 450 nm) of the liquid reaction mixture, i.e., using the equation: degree of adsorption (%)=[1−(absorbance of liquid reaction mixture)/(absorbance of liquid reaction mixture obtained without anion-exchange resin)]×100. The "absorbance of liquid reaction mixture obtained without anion-exchange resin" was the simple average of the absorbances of several liquid reaction mixture samples differing in conversion and obtained through the same reaction except that no anion-exchange resin was used.

The results of the reaction obtained are shown in Table 1. After the reaction, the volume of the resin A was 4.9 ml (23 vol % based on the whole liquid reaction mixture). The selectivity to hydroxypropyl acrylate (HPA; target compound) at 5.5 hours after initiation of the reaction was 96.3 mol % (based on AA).

The reaction mixture was subjected to vacuum filtration, whereby the resin A which had assumed a dark green color (light-yellow before the reaction) and a liquid reaction mixture which was light-green (dark-green before the reaction) were obtained. It was concluded from the results in Table 1 that the chromium catalyst is gradually adsorbed onto the anion-exchange resin with progress of the reaction and is separated and recovered. The degree of adsorption in the final liquid reaction mixture was determined by ICP emission spectroscopy and was found to be 96%. This value almost agreed with the value obtained from absorbance.

TABLE 1

| Reaction time | Conversion of AA | Degree of adsorption of chromium ion onto anion-exchange resin |
| --- | --- | --- |
| 4 hrs | 95.5% | 72% |
| 5 hrs | 98.9% | 89% |
| 5.5 hrs | 99.7% | 95% |

Comparative Example 1

An experiment was conducted in completely the same manner as in Example 1, except that the resin A was not introduced into the reactor. The results obtained are shown in Table 2. The selectivity to HPA at 4.5 hours after initiation of the reaction was 95.7 mol %. After the reaction, the liquid reaction mixture was dark-green.

TABLE 2

|  | Reaction time | Conversion of AA | Degree of adsorption of chromium ion |
| --- | --- | --- | --- |
| Comparative Example 1 | 2 hrs | 74.9% | 0% |
|  | 4 hrs | 93.8% | −1% |
|  | 4.5 hrs | 98.3% | 1% |

Example 2

An experiment was conducted in completely the same manner as in Example 1, except that the amount of chromium(III) acetate was changed to 120 mg. The results obtained are shown in Table 3. The selectivity to HPA at 2.5 hours after initiation of the reaction was 97.3 mol %. The reaction mixture was subjected to vacuum filtration, whereby the resin A which had assumed a dark green color and a light-green liquid reaction mixture were obtained. The increase in chromium catalyst amount resulted in a reduction in reaction time and an improvement in selectivity. Furthermore, use of the anion-exchange resin in combination with the catalyst enabled the recovery of chromium ions.

Example 3

An experiment was conducted in completely the same manner as in Example 2, except that the amount of the resin A was changed to 2.0 g. The results obtained are shown in Table 3. The selectivity to HPA at 3 hours after initiation of the reaction was 97.9 mol %. After the reaction, the volume of the resin A was 14.3 ml. The increase in resin amount resulted in improvements in the degree of adsorption of chromium ions and in selectivity to HPA.

Example 4

An experiment was conducted in completely the same manner as in Example 2, except that the anion-exchange resin was replaced with 1.09 g of DIAION TSA1200 (manufactured by Mitsubishi Chemical Corp.; styrene-based anion-exchange resin having as exchange groups quaternary ammonium salt groups bonded to the matrix through butylene groups; having high heat resistance; used as a chloride ion type dry resin) and that the reaction temperature was changed to 50° C. The results obtained are shown in Table 3. The selectivity to HPA at 5 hours after initiation of the reaction was 97.4 mol %. The reaction mixture was subjected to vacuum filtration, whereby TSA1200 which had assumed a dark green color and a light-green liquid reaction mixture obtained. After the reaction, the volume of the TSA1200 was 4.9 ml. It was thus found that the effects of the invention are obtained even with the commercial ion-exchange resin of the quaternary ammonium salt type.

Example 5

An experiment was conducted in completely the same manner as in Example 4, except that the anion-exchange resin was replaced with 0.78 g of an anion-exchange resin B (the anion-exchange resin disclosed in the Example 1 of Japanese Patent Application No. 2000-181265; produced by solidifying diallyldimethylammonium chloride by copolymerizing it with a crosslinking agent; having high heat resistance; used as a chloride ion type dry resin). The results obtained are shown in Table 3. The selectivity to HPA at 6 hours after initiation of the reaction was 97.2 mol %. The reaction mixture was subjected to vacuum filtration, whereby the resin B which had assumed a dark green color and a light-green liquid reaction mixture were obtained. After the reaction, the volume of the resin B was 5.0 ml.

Example 6

An experiment was conducted in completely the same manner as in Example 4, except that the anion-exchange resin was replaced with 0.57 g of a tertiary amine type anion-exchange resin C (the anion-exchange resin disclosed in the Example 5 of Japanese Patent Laid-Open No. 2000-070724; produced by polymerizing triallylamine hydrochloride; used as a free amine type dry resin). The results obtained are shown in Table 3. The selectivity to HPA at 6 hours after initiation of the reaction was 97.2 mol %. The reaction mixture was subjected to vacuum filtration, whereby the resin C which had assumed a dark green color and a light-green liquid reaction mixture were obtained. After the reaction, the volume of the resin C was 5.8 ml. It was thus found that the effects of the invention are obtained even with the tertiary amine type anion-exchange resin.

TABLE 3

|  | Reaction time | Conversion of AA | Degree of adsorption of chromium ion onto anion-exchange resin |
|---|---|---|---|
| Example 2 | 2 hrs | 97.7% | 75% |
|  | 2.5 hrs | 99.9% | 91% |
| Example 3 | 2 hrs | 96.5% | 85% |
|  | 3 hrs | 99.6% | 97% |

TABLE 3-continued

|  | Reaction time | Conversion of AA | Degree of adsorption of chromium ion onto anion-exchange resin |
|---|---|---|---|
| Example 4 | 4 hrs | 96.8% | 74% |
|  | 5 hrs | 99.4% | 91% |
| Example 5 | 4 hrs | 92.6% | 57% |
|  | 6 hrs | 99.3% | 91% |
| Example 6 | 4 hrs | 90.4% | 76% |
|  | 6 hrs | 98.9% | 86% |

Example 7

Into a reactor were introduced 120 mg of chromium acetate, 10.0 g of acrylic acid (AA), and 8.6 g of propylene oxide (PO) (PO/AA molar ratio=1.1). Reaction was initiated at 70° C. without adding a resin. At the time when the reaction had been conducted for 1 hour, 0.78 g of the anion-exchange resin B (chloride ion type dry resin) was introduced into the reactor to further conduct the reaction. The results of the reaction are shown in Table 4. Although contact with the resin was initiated in the course of the reaction, the adsorption of chromium ions occurred satisfactorily.

TABLE 4

| Reaction time | Conversion of AA | Degree of adsorption of chromium ion onto anion-exchange resin |
|---|---|---|
| 1 hr | 84.7% | 0% |
| 4 hrs | 99.6% | 97% |
| 4.8 hrs | 99.9% | 99% |

Example 8

An experiment was initiated in completely the same manner as in Example 2. At 3.2 hours after initiation of the reaction, the conversion of the AA reached 100.0% and the degree of adsorption of chromium ions was 99%. Subsequently, a 15.0 g portion of the liquid reaction mixture only was taken out of the reaction mixture with a pipet, and 7.5 g each of acrylic acid (AA) and propylene oxide (PO) were added thereto. Upon addition of the AA, chromium ions were liberated, making the liquid reaction mixture green. Reaction was conducted again while shaking the resultant mixture at 60° C. The same operation was repeated to examine suitability for reuse. The results obtained are shown in Table 5. The progress of the reaction was followed by monitoring the absorbance. At the time when the degree of adsorption reached 95% or higher, the reaction was terminated. It was thus found that the chromium catalyst adsorbed on the anion-exchange resin can be easily reused.

TABLE 5

| Number of batches | Reaction time | Conversion of AA | Degree of adsorption of chromium ion onto anion-exchange resin |
|---|---|---|---|
| 1 | 3.2 hrs | 100.0% | 99% |
| 2 | 3.0 hrs | 100.0% | 99% |
| 3 | 3.0 hrs | 100.0% | 99% |
| 4 | 3.0 hrs | 100.0% | 98% |
| 5 | 3.1 hrs | 100.0% | 98% |
| 6 | 3.1 hrs | 100.0% | 99% |

Example 9

A reuse experiment was conducted in completely the same manner as in Example 8, except that the anion-exchange resin was replaced with 1.09 g of DIAION TSA1200, which was used in Example 4. The results obtained are shown in Table 6. It was thus found that the chromium catalyst adsorbed on TSA1200 also can be easily reused. Furthermore, after completion of the six batches, the TSA1200 was examined for anion-exchange capacity. As a result anion-exchange capacity of the TSA1200 was found to remain unchanged.

TABLE 6

| Number of batches | Reaction time | Conversion of AA | Degree of adsorption of chromium ion onto anion-exchange resin |
|---|---|---|---|
| 1 | 3.8 hrs | 100.0% | 99% |
| 2 | 3.3 hrs | 100.0% | 99% |
| 3 | 3.0 hrs | 100.0% | 98% |
| 4 | 3.2 hrs | 100.0% | 99% |
| 5 | 2.9 hrs | 99.9% | 95% |
| 6 | 3.1 hrs | 100.0% | 97% |

Example 10

A reuse experiment was conducted in completely the same manner as in Example 8, except that the anion-exchange resin was replaced with 0.78 g of the resin B used in Example 6. The results obtained are shown in Table 7. It was thus found that the chromium catalyst adsorbed on the resin B also can be easily reused. Furthermore, after completion of six batches, the resin B was examined for anion-exchange capacity. As a result, the anion-exchange capacity of the resin B was found to remain unchanged.

TABLE 7

| Number of batches | Reaction time | Conversion of AA | Degree of adsorption of chromium ion onto anion-exchange resin |
|---|---|---|---|
| 1 | 3.8 hrs | 100.0% | 99% |
| 2 | 3.1 hrs | 100.0% | 100% |
| 3 | 2.8 hrs | 100.0% | 99% |
| 4 | 2.8 hrs | 100.0% | 99% |
| 5 | 2.6 hrs | 99.9% | 96% |
| 6 | 2.9 hrs | 100.0% | 99% |

Example 11

An experiment was conducted in completely the same manner as in Example 1, except that the soluble metallic catalyst was replaced with 84 mg of iron(III) nitrate nonahydrate and the reaction temperature was changed to 70° C.

At 2 hours after initiation of the reaction, the conversion of the AA was 74.7% and the degree of adsorption of iron ions onto the anion-exchange resin was 57%. At 4 hours after the initiation, the conversion of the AA was 91.5% and the degree of adsorption was 78%. At 7 hours after the initiation, the conversion of the AA reached 98.5% and the degree of adsorption was 88%. The reaction mixture was subjected to vacuum filtration, whereby the resin A which had assumed a brown color and a light-brown liquid reaction mixture were obtained. It was thus found that the iron compound also can be easily recovered by the invention.

Comparative Example 2

An experiment was conducted in completely the same manner as in Example 11, except that the anion-exchange resin was not introduced into the reactor. At 4 hours after initiation of the reaction, the conversion of the AA was 85.0%. At 7 hours after the initiation, the conversion of the AA reached 97.3%, but the absorbance of the liquid reaction mixture and the degree of adsorption were 1.10 and 0%, respectively. After the reaction, the liquid reaction mixture was dark-brown.

Example 12

Next, a reaction for forming a hydroxypropyl ester was conducted using acetic acid as a carboxylic acid to examine the effects of the invention. Namely, an experiment was conducted in the same manner as in Example 1, except that the acrylic acid was replaced with 8.3 g of acetic acid and the reaction temperature was changed to 70° C. The results obtained are shown in Table 8. Furthermore, the reaction mixture was subjected to vacuum filtration, whereby the resin A which had assumed a dark green color and a light-green liquid reaction mixture were obtained.

Example 13

An experiment was conducted in completely the same manner as in Example 12, except that the carboxylic acid was replaced with 10.3 g of propionic acid. The results obtained are shown in Table 8. Furthermore, the reaction mixture was subjected to vacuum filtration, whereby the resin A which had assumed a dark green color and a light-green liquid reaction mixture were obtained.

Example 14

An experiment was conducted in completely the same manner as in Example 12, except that the carboxylic acid was replaced with 12.2 g of n-butyric acid. The results obtained are shown in Table 8. Furthermore, the reaction mixture was subjected to vacuum filtration, whereby the resin A which had assumed a dark green color and a light-green liquid reaction mixture were obtained.

Example 15

An experiment was conducted in completely the same manner as in Example 12, except that the amount of chromium acetate was changed to 40 mg and the carboxylic acid was replaced with 11.9 g of methacrylic acid. The results obtained are shown in Table 8.

Example 16

An experiment was conducted in completely the same manner as in Example 12, except that the carboxylic acid was replaced with 11.9 g of methacrylic acid and the reaction temperature was changed to 60° C. The results obtained are shown in Table 8. However, at the time when the reaction had been conducted for 4.5 hours and the conversion had reached 100%, 110 mg of acetic acid was introduced into the reactor to continue the reaction for further 30 minutes. Throughout this 30-minute period, the selectivity to hydroxypropyl methacrylate remained unchanged. As a result of this 30-minute reaction, the degree of adsorption was improved. Furthermore, the reaction mixture was subjected to vacuum filtration, whereby the resin A which had assumed a dark green color and a light-green liquid reaction mixture were obtained. It was found that as compared with Example 15, the degree of adsorption was improved by the addition of acetic acid.

TABLE 8

|  | Kind of carboxylic acid | Reaction time | Conversion of carboxylic acid | Degree of adsorption of chromium ion onto anion-exchange resin |
|---|---|---|---|---|
| Example 12 | Acetic acid | 2 hrs | 71.8% | 66% |
|  |  | 3.5 hrs | 87.6% | 82% |
|  |  | 6 hrs | 98.3% | 96% |
| Example 13 | Propionic acid | 2 hrs | 98.2% | 72% |
|  |  | 2.5 hrs | 99.9% | 92% |
| Example 14 | n-Butyric acid | 2 hrs | 99.5% | 59% |
|  |  | 2.5 hrs | 100.0% | 93% |
| Example 15 | Methacrylic acid | 3 hrs | 100.0% | 71% |
|  |  | 3.5 hrs | 100.0% | 80% |
|  |  | 4 hrs | 100.0% | 83% |
| Example 16 | Methacrylic acid | 4.5 hrs | 100.0% | 77% |
|  |  | 5 hrs | 100.0% | 96% |

Example 17

Next, the effects of the invention were examined in a reaction for forming the hydroxyethyl ester of acrylic acid using chromium(III) acetate as a soluble metallic catalyst. First, 180 g of acrylic acid (AA), 2.2 g of chromium acetate, 8.0 g of the resin B used in Example 5, and a polymerization inhibitor were introduced into a 500 ml autoclave. The autoclave was closed and the contents were heated to 60° C. Subsequently, 120 g of ethylene oxide (EO) was added thereto over 2 hours and the reaction was continued further. The analysis of a liquid reaction mixture and the determination of the degree of adsorption were made in the same manner as in Example 1. The results obtained are shown in Table 9. At 4.5 hours after initiation of the reaction, the selectivity to 2-hydroxyethyl acrylate (HEA) was 94 mol %. Furthermore, the reaction mixture after the reaction was subjected to vacuum filtration, whereby the resin B which had assumed a dark green color and a light-green liquid reaction mixture were obtained. It was found that the effects of the invention are obtained also in the reaction for forming the hydroxyethyl ester of acrylic acid.

Comparative Example 3

An experiment was conducted in the same manner as in Example 17, except that the amount of chromium acetate was changed to 1 g and the resin A was not introduced into the autoclave, and that ethylene oxide (EO) was added over 4 hours. At the time when the reaction had been conducted for 6.5 hours in total, the conversion of the AA reached 100.0% and the selectivity to HEA was 93 mol %. The recovery of chromium ions was, of course, impossible and the liquid reaction mixture was dark-green.

Example 18

A reaction was conducted in completely the same manner as in Example 17. At 4 hours after initiation of the reaction, 1.1 g of succinic acid was introduced into the reactor to further continue the reaction. The results obtained are shown in Table 9. Due to the addition of succinic acid, the degree of adsorption of chromium ions at an AA conversion of 100.0% increased to 96%.

Example 19

In the same manner as in Example 17, 1.6 g of chromium acetate, 130 g of acrylic acid (AA), 5.8 g of the resin B, and 92 g of methyl ethyl ketone as a solvent were introduced into an autoclave and the contents were heated to 60° C. Subsequently, 84 g of ethylene oxide (EO) was added thereto over 2 hours and the reaction was continued further. The results obtained are shown in Table 9. At 7 hours after initiation of the reaction, the selectivity to HEA was 96 mol %. It was thus found that due to the addition of the solvent, the degree of adsorption of chromium ions and selectivity to HEA at an AA conversion of 100% are improved.

TABLE 9

|  | Reaction time | Conversion of AA | Degree of adsorption of chromium ion onto anion-exchange resin |
|---|---|---|---|
| Example 17 | 4 hrs | 99.8% | 53% |
|  | 4.5 hrs | 100.0% | 91% |
|  | 5 hrs | 100.0% | 92% |
| Example 18 | 4 hrs | 99.9% | 65% |
|  | 4.5 hrs | 99.9% | 85% |
|  | 5 hrs | 100.0% | 96% |
| Example 19 | 5 hrs | 99.3% | 69% |
|  | 6 hrs | 99.8% | 87% |
|  | 6.5 hrs | 99.9% | 93% |
|  | 7 hrs | 100.0% | 97% |

Example 20

An experiment was conducted in the same manner as in Example 17, except that the acrylic acid (AA) was replaced with 200 g of methacrylic acid (MA) and the amount of chromium acetate was changed to 1.4 g and that 9 g of the resin A used in Example 1 was added as an anion-exchange resin. Ethylene oxide (EO) was added in an amount of 110 g over 3 hours. At 5.5 hours after initiation of the reaction, the conversion of the MA reached 100.0% and the degree of adsorption of chromium ions onto the anion-exchange resin was 65%. Furthermore, the reaction mixture after the reaction was subjected to vacuum filtration, whereby the resin A which had assumed a dark green color and a light-green liquid reaction mixture were obtained.

While the invention has been described in detail and with reference to specific embodiments thereof, it will be apparent to one skilled in the art that various changes and modifications can be made therein without departing from the spirit and scope thereof.

This application is based on a Japanese patent application filed on Mar. 26, 2001 (Patent Application No. 2001-087846), the contents thereof being hereby incorporated by reference.

INDUSTRIAL APPLICABILITY

According to the invention, by using a soluble metallic catalyst in combination with an anion-exchange resin in liquid-phase reactions, the soluble metallic catalyst used can be recovered from the reaction system with great ease at low cost. Furthermore, the soluble metallic catalyst recovered can be reused without necessitating any complicated treatment. Therefore, neither an adsorption step which is time-consuming and complicated nor a desorption step is necessary and, hence, a simple catalyst-recycling system can be established.

What is claimed is:

1. A batch method of liquid-phase reaction of a carboxylic acid with an epoxy compound to produce a hydroxy ester of the carboxylic acid using a soluble metallic catalyst in a liquid reaction mixture which comprises causing the soluble metallic catalyst to coexist with an anion-exchange resin during the reaction and conducting the reaction under such conditions that 50% or more of the soluble metallic catalyst is adsorbed onto the anion-exchange resin, which further includes the step of separating the anion-exchange resin having the soluble metallic catalyst adsorbed thereon from the liquid reaction mixture and recovering the soluble metallic catalyst.

2. The method of reaction of claim 1, which further includes the step of reusing in the liquid-phase reaction the anion-exchange resin having the soluble metallic catalyst adsorbed thereon.

3. The method of reaction of claim 1, wherein (meth) acrylic acid is reacted with an epoxy compound to produce a hydroxyl ester of (meth)acrylic acid.

4. The method of reaction of claim 3, wherein (meth) acrylic acid is reacted with ethylene oxide to produce hydroxyethyl (meth)acrylate.

5. The method of reaction of claim 1, wherein the anion-exchange resin comprises at least one resin selected from the group consisting of a resin containing an amine and/or a quaternary ammonium salt, a resin containing pyridine and/or a pyridinium salt, and a resin containing a phosphine arid/or a quaternary phosphonium salt.

6. The method of reaction of claim 1, wherein the soluble metallic catalyst comprises a compound containing at least one metallic element selected from the group consisting of chromium, iron, tin, manganese, cobalt, vanadium, titanium, nickel, zinc, copper, zirconium, molybdenum, tungsten, aluminum, lead, indium, ruthenium, rhodium, palladium, platinum, gold, and silver.

7. The method of reaction of claim 1, which includes the step of improving the degree of adsorption of the soluble metallic catalyst onto the anion-exchange resin by conducting at least one method selected from the group consisting of a method in which the conversion of a starting material is heightened to lower the concentration of the starting material, a method in which an ingredient forming a more stable complex is added, and a method in which a solvent is added.

8. The method of reaction of claim 1, wherein the soluble metallic catalyst and the anion-exchange resin are caused to coexist in a single reactor and the reaction and adsorption are conducted therein.

9. The method of reaction of claim 1, wherein the reaction occurs in a reaction vessel and another vessel containing the anion-exchange resin is separately arranged and the liquid reaction mixture containing the soluble metallic catalyst is circulated through the another vessel, whereby the soluble metallic catalyst is absorbed on the anion-exchange resin.

* * * * *